United States Patent
Dunshee et al.

(10) Patent No.: US 6,905,732 B1
(45) Date of Patent: Jun. 14, 2005

(54) ABRASION-RESISTANT INK COMPOSITIONS AND METHODS OF USE

(75) Inventors: Wayne K. Dunshee, Maplewood, MN (US); Mary Lynn Brown, St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/577,551

(22) Filed: May 24, 2000

Related U.S. Application Data

(62) Division of application No. 08/949,903, filed on Oct. 15, 1997, now abandoned.

(51) Int. Cl.[7] .......................... A61F 13/00; A61F 15/00; B05D 3/02; B32B 27/00; B32B 27/40
(52) U.S. Cl. ................ 427/372.2; 427/385.5; 427/393.5; 428/423.1; 602/41; 602/54; 602/55; 602/58
(58) Field of Search .......................... 427/372.2, 385.5, 427/393.5; 428/423.1; 602/41, 54, 55, 58

(56) References Cited

U.S. PATENT DOCUMENTS

| | | | |
|---|---|---|---|
| 2,532,011 A | 11/1950 | Dahlquist et al. ........... 154/53.5 |
| 2,607,711 A | 8/1952 | Hendricks ................. 117/122 |
| 3,011,988 A | 12/1961 | Luedke et al. ............. 260/29.6 |
| 3,318,852 A | 5/1967 | Dixon ........................ 260/78.5 |
| 3,645,835 A | 2/1972 | Hodgson .................... 161/146 |
| 3,694,241 A | 9/1972 | Guthrie et al. | |
| 3,728,298 A | 4/1973 | Hartmann .................. 260/31.4 |
| 4,147,679 A | 4/1979 | Scriven et al. ............. 260/29.2 |
| 4,156,067 A | 5/1979 | Gould ........................ 528/73 |
| 4,231,911 A | 11/1980 | Santiago | |
| 4,301,053 A | 11/1981 | Wolfrey .................... 260/29.9 |
| 4,334,530 A | * 6/1982 | Hassell | |
| 4,337,183 A | 6/1982 | Santiago .................... 524/446 |
| 4,433,095 A | 2/1984 | Hombach et al. .......... 524/563 |
| RE31,887 E | 5/1985 | Hodgson .................... 428/355 |
| 4,540,633 A | 9/1985 | Kucera et al. ........... 428/423.1 |
| 4,612,052 A | 9/1986 | Schwartz | |
| 4,663,377 A | 5/1987 | Hombach et al. ........... 524/196 |
| 4,704,163 A | 11/1987 | Baratto et al. .............. 106/20 |
| 4,812,492 A | 3/1989 | Eckes et al. ................ 523/351 |
| 4,851,459 A | 7/1989 | Ramalingam | |
| 4,963,188 A | 10/1990 | Parker | |
| 4,965,126 A | 10/1990 | Abraham et al. ........... 428/343 |
| 5,162,141 A | * 11/1992 | Davey et al. | |
| 5,173,111 A | 12/1992 | Krishnan et al. ............. 106/20 |
| 5,230,701 A | 7/1993 | Meyer et al. ................ 602/76 |
| 5,462,768 A | 10/1995 | Adkins et al. .............. 427/265 |
| 5,494,960 A | 2/1996 | Rolando et al. | |
| 5,531,855 A | 7/1996 | Heinecke et al. ........... 156/252 |
| 5,532,058 A | 7/1996 | Rolando et al. | |
| 5,656,701 A | 8/1997 | Miyamoto et al. .......... 525/453 |

FOREIGN PATENT DOCUMENTS

| | | |
|---|---|---|
| CA | 2073115 | 1/1993 |
| DE | 196 39 755 C1 | 9/1996 |
| DE | 295 18 174 U1 | 2/1997 |
| EP | 0 255 078 A2 | 2/1988 |
| EP | 0360212 | 3/1990 |
| EP | 0522420 | 1/1993 |
| EP | 0 358 712 B1 | 4/1994 |
| EP | 596503 * | 5/1994 |
| EP | 0596503 | 5/1994 |
| FR | 2 440 588 | 5/1980 |
| FR | 2 544 982 A | 11/1984 |
| GB | 2 042 976 A | 10/1980 |
| JP | 49-133467 | 12/1974 |
| WO | WO 88/08787 | 11/1988 |
| WO | 93/03103 | 2/1993 |

* cited by examiner

*Primary Examiner*—Patrick D. Niland

(57) ABSTRACT

This invention relates to ink compositions that includes a stable nonpolyethylene-containing aqueous dispersion of pigment and particles of a urethane polymer Preferably the composition further includes a cross-linker capable of cross-linking the urethane polymer. The compositions are useful for printing on flexible or elastomeric substrates. These ink compositions demonstrate increase durability, in particular abrasion resistance, abrasion resistance during stretch and water resistance.

40 Claims, 1 Drawing Sheet

ABRASION-RESISTANT INK COMPOSITIONS AND METHODS OF USE

This is a divisional of Application Ser. No. 08/949,903 filed Oct. 15, 1997 now abandoned.

FIELD OF THE INVENTION

The present invention relates to printing ink compositions and in particular the invention relates to printing ink for flexible or elastomeric substrates.

BACKGROUND OF THE INVENTION

Flexible or elastomeric substrates are used in a variety of applications. For example, tapes, bandages, coverings, labels, food packaging and the like are often prepared from flexible or elastomeric substrates. Pressure-sensitive adhesive webs are one example of a flexible or elastomeric substrate that is used to form tapes for joining, mending, masking, sealing, splicing, protecting, reinforcing, identifying and as part of fabrics or for home decorating items. Pressure-sensitive adhesive webs are often employed as coverings for walls, and the like. Flexible or elastomeric substrates are typically prepared from materials such as polyester, polyethylene, polyurethane, polypropylene, non-woven elastomeric webs, such as those disclosed in U.S. Pat. No. 5,230,701 to Meyer, et al. and ionomers.

In many applications of flexible or elastomeric substrates, it is desirable to have a printed message or design on an exposed surface, generally on the adhesive-free side of the substrate where the substrate comprises a surface having adhesive positioned thereon. Inks typically include hard, waxy components and the integrity of the ink when printed onto a flexible surface, and particularly an elastomeric surface, can therefore be a problem. For example, many inks when printed on a flexible surface shatter or otherwise breakdown and many flexible surfaces do not bind well to the inks. Moreover, maintaining the integrity of the ink when printed onto a porous elastic (such as the substrate taught by Meyer et al. U.S. Pat. No. 5,230,701) or flexible surface such as can be a problem. Many types of inks do not bind well to porous elastic or flexible surfaces. Breakage of the ink resulting from the flexibility of the surface or the porous nature of the surface can reduce the durability of the ink. In addition, when some commonly available inks are used for printing, the inks tend to rub-off either onto an adjoining surface, such as when a flexible or elastomeric substrate is coated with an adhesive and another side is coated with a low adhesion backsizing (LAB) or through rubbing or manipulation of the printed surface, such as can occur with some tapes, such as packaging tapes or bandages.

A common procedure in handling a pressure-sensitive adhesive web is to wind it in a roll with adjacent contact between adhesive-coated and adhesive-free sides with the web being unwound prior to use. In order to facilitate unwinding of this roll, the adhesive-free side of the web is usually coated with an appropriate "low adhesion" or release coating, often termed a low adhesion backsize or LAB. These coatings do not assist in abrasion resistance to a great extent, particularly for applications where the substrate is exposed to extensive abrasion, flexing, elevated temperatures, and the like.

Inks having low rub-off properties are known in the prior art. Attempts have been made to modify ink by the addition of natural or synthetic waxy materials, but these additives tend to migrate into an adhesive when used in a roll of pressure-sensitive adhesive webbing or easily rub-off with mild abrasion. Durability of inks has been manipulated by the addition of waxes or resins. Inks with wax can exhibit improved mar resistance, slip and water repellency properties. Wax of a controlled fine particle size can be mixed or ground into the batch along with pigments or may be introduced during the final blending operations. Alternatively, the wax can be compounded into a "wax media" by dispersing or melting the wax into the varnishes and/or solvents and adding these to the ink.

It is generally known that non-rub qualities imparted by an individual wax are a function of both the particle size and the hardness as well as the melting temperature of a particular wax. However, addition of waxes to inks to impart non-rub qualities to an ink introduces other problems, particularly for printed flexible or elastomeric substrates. For example, with wax, the heat and movement imparted by abrasion on a printed flexible or elastomer surface can result in particles in the film balling up and creating unprinted areas. Increased amount of wax added to improve rub resistance causes problems related to the hardness and the gloss of the printed ink. The addition of wax to ink almost invariably decreases their gloss and a glossy printed image tends to be more visible and therefore, more desirable for many applications. In addition, the use of some waxes, such as microcrystalline or polytetrafluoroethylene waxes are expensive, resulting in increased cost in the production process.

Synthetic waxes such as polyethylene waxes and polytetrafluoroethylene waxes are used in the ink industry. Such waxes are often added as a "non-rub" or a "slip" medium. This medium is generally a fine dispersion of wax in the ink solvent, oil or resin that is compatible with the ink formulation in which it is to be added. Waxes prepared from polytetrafluoroethylene powders can be used in a variety of printing inks, but are particularly useful for heatset inks, where the temperature of the drying apparatus does not cause them to soften or melt. Polytetrafluoroethylene-based waxes can also be stirred into finished inks to improve rub and scuff resistance. Nevertheless, the relative cost of a polytetrafluoroethylene wax is prohibitively high form many applications.

The term "abrasion resistance" can be used in the ink art to refer to the ability of an ink to minimize its damage to the printing plates, such as those used in the gravure printing process. For example, U.S. Pat. No. 5,173,111 to Krishnan et al. discloses an abrasion resistant printing ink that incorporates alkoxylated dibasic phosphate esters and an alkali metal salt of a dialkylsulfosuccinic ester as a method for decreasing wear on printing plates and thereby reducing the need for resurfacing of the plates.

Alternatively, abrasion resistance is also used in the ink art to refer to the ability of an ink composition to resist wear on the printed substrate. For example, U.S. Pat. No. 4,704,163 uses a synthetic polymeric low adhesion backsize compound, such as polyvinyl N-octadecyl carbamate, as an additive to flexographic ink to protect the print on rolled tape from lifting off when the tape is unrolled.

U.S. Pat. No. 4,337,183 to Santiago discloses a printing composition comprising a polyurethane and a polyethylene resin. The polyurethane in this composition functions as a hard resin binder for a lubricity aid. While Santiago indicates that the compositions can be used to print onto metals or plastics, the compositions would not be useful for many flexible substrates and would not be useful on elastomeric substrates.

There remains a need for cost-effective, wear-resistant inks suitable for use on flexible or elastomeric substrates.

SUMMARY OF THE INVENTION

Figure 1:
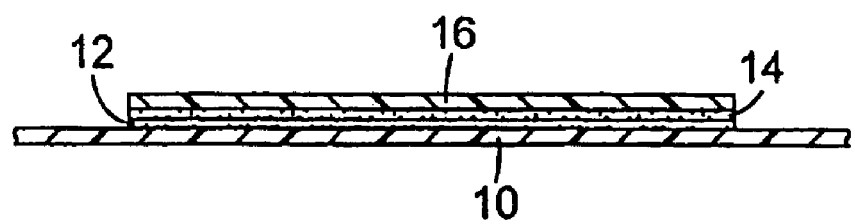
FIG. 1 is a cross-section of the ink compositions of this invention on a flexible or elastomeric substrate.

The present invention relates to ink compositions that are useful for printing on a flexible or elastomeric substrate. The ink compositions demonstrate improved durability as measured by resistance to abrasion, including resistance to abrasion following stretch. In a preferred ink composition of this invention, the ink composition comprises a stable nonpolyethylene-containing aqueous dispersion of pigment and particles of a urethane polymer. Preferably the ink composition further comprises a cross-linker capable of cross-linking the urethane polymer and in one embodiment the pigment particles comprise a white pigment. In one embodiment, the pigment includes particles present in least about 1% by weight of the ink composition. The ink compositions can be used in a variety of printing methods including flexographic printing.

The invention also relates to ink compositions comprising a stable nonpolyethylene-containing aqueous dispersion of pigment, particles of a urethane polymer and a cross-linker to cross-link the urethane polymer.

In another aspect of this invention, the invention also relates to a liquid ink composition comprising about 1% to about 60% by weight of pigment particles based on the total weight of the ink composition and about 5% to about 99% by weight of particles of a urethane polymer based on the total weight of the ink composition. Preferably the ink composition further comprising less than about 2.5% by weight of a cross-linker based on the total weight of the ink composition, wherein the cross-linker cross-links the polyurethane. In still another embodiment, the ink composition comprises about 58% to about 93% by weight of particles of a urethane polymer based on the total weight of the ink composition. Also preferably, the ink composition comprises about 5% to about 40% by weight of pigment particles and about 58% to about 93% by weight of particles of a urethane polymer based on the total weight of the ink composition.

In another aspect of this invention, a method for improving durability of an image on a flexible substrate is disclosed, comprising the step of coating a layer of a urethane polymer containing composition onto a flexible substrate suitable for printing an image wherein the urethane polymer comprises a number average molecular weight in the noncross-linked form of about 1,500 to about 50,000. Preferably the urethane polymer-containing composition is an ink composition comprising a dispersion of pigment and in another embodiment, the urethane polymer-containing compound further comprises a cross-linker to cross-link the urethane polymer. In one aspect of this embodiment, the urethane polymer-containing compound is coated onto the flexible substrate prior to printing the image and in yet another embodiment, the urethane polymer-containing compound is coated over the image on the flexible substrate.

The invention also relates to a method for printing an image on a flexible or elastomeric substrate comprising the step of printing an image using at least one ink composition comprising a stable nonpolyethylene containing aqueous dispersion of pigment and particles of a urethane polymer. This method can further comprise the step of coating a layer of a urethane polymer-containing composition onto the flexible or elastomeric substrate before the printing step. In one embodiment, the urethane polymer comprises a number average molecular weight in the noncross-linked form of about 1,500 to about 50,000 and in another embodiment, the urethane polymer-containing compound of the coating step further comprises a cross-linker to cross-link the urethane polymer. Preferably the ink composition further comprises a cross-linker to cross-link the urethane polymer and preferably the ink composition is provided in at least one layer of ink in the printed image. Also preferably, at least one layer of ink comprises a dispersion of white pigment and preferably the ink composition of this method is present in the last ink layer printed in the image.

In another method, the invention relates to a method for printing an image on an elastomeric substrate comprising the steps of printing a first layer of ink onto an elastomeric substrate, the first layer of ink comprising a stable aqueous dispersion of pigment and particles of a urethane polymer and printing an image over the first layer of ink wherein the last layer of ink, farthest from the substrate, comprises a stable aqueous dispersion of pigment and particles of a urethane polymer. Preferably at least one layer of ink is printed using a nonaqueous-based ink and preferably the ink composition in the first layer of ink further comprises a cross-linker to cross-link the urethane polymer. Also preferable, the first layer comprises an ink comprising a white pigment. In a preferred embodiment of this method, an opaque layer of white pigment is disposed between the first layer of ink and the image. Preferably the image is printed with an ink composition comprising a stable aqueous dispersion of pigment and particles of a urethane polymer and preferably the last layer of ink, farthest from the substrate, further comprises a cross-linker to cross-link the urethane polymer. In one embodiment of this method, the image is covered with a coating comprising a backsize or sealer and preferably the sealer is a urethane polymer adhesive.

In another preferred aspect of this method, the flexible or elastomeric substrate is formed as a bandage. A bandage preferably comprises an elastomeric substrate and an adsorbent pad. Preferably the image is printed over the adsorbent pad. In a preferred embodiment of this method, the flexible substrate is selected from a group consisting of polyurethane, elastomeric polyethylene, low density polyethylene and a nonwoven elastomeric web. In another preferred embodiment, the flexible or elastomeric substrate is formed as a balloon, label, sticker, elastomeric sheet, stretch band, temporary tattoo, or adhesive tape.

In another method of this invention, the invention relates to a method for limiting abrasion of an ink on a flexible substrate comprising the steps of applying a composition comprising a water-based dispersion of a urethane polymer to a flexible surface, and printing an image over the composition using at least one ink composition. Preferably, the composition is an ink composition comprising a stable aqueous dispersion of pigment and particles of a urethane polymer and a cross-linker to cross-link the urethane polymer and preferably the at least one ink composition of the printing step comprises a stable aqueous dispersion of pigment and particles of a urethane polymer and a cross-linker to cross-link the urethane polymer. In a preferred embodiment, the printing step is selected from the group consisting of rotogravure printing, flexographic printing and offset printing and in another preferred embodiment, the flexible substrate is selected from a group consisting of polyurethane, elastomeric polyethylene, low density polyethylene, and a nonwoven elastomeric web. In one aspect of this method, the composition comprises a water-based pigment and preferably, the water-based pigment is a white pigment.

In another aspect of this invention, the invention relates to an ink composition preparable by combining components comprising a liquid carrier, a water based pigment dispersion and a water-based urethane polymer, wherein the components are sufficient compatible to form a stable dispersion. Preferably, the ink composition comprises a cross-linker to cross-link the urethane polymer and the urethane polymer comprises a urethane having a number average molecular weight in the noncross-linked form of about 1,500 to about 50,000.

The invention also relates to an elastomeric bandage comprising a printed image wherein the printed image is prepared from at least one ink composition comprising a stable aqueous dispersion of pigment and particles of a urethane polymer. Preferably the at least one ink composition further comprises a cross-linker to cross-link the urethane polymer and preferably the bandage further comprises a pad. Where the bandage comprises a pad, preferably the image is printed over the pad.

DETAILED DESCRIPTION OF THE INVENTION

This invention relates to a printing ink composition and to methods for printing using the inks of the present invention and to a method for improving the durability of the ink on a printed flexible or printed elastomeric substrate, such as for example, a film laminate, particularly a thin film laminate such as a tape, a bandage, food packaging, coatings on fabrics, and the like. The flexible or elastomeric substrate can be prepared from a variety of materials including polyester, elastomeric polyethylene, low density polypropylene, ionomers and polyurethane. Ink durability, as used herein, refers to improved abrasion resistance, durability of the ink with stretch, and deformation and improved water-resistance. An elastomeric substrate refers to substrates that can be stretched or deformed to least an additional 5% of their length in at least one dimension.

In a first embodiment of the invention, the invention comprises a printing ink composition. In one embodiment, the printing ink composition of the present invention comprises a stable aqueous dispersion of pigment and particles of a urethane polymer. Preferably, the printing composition comprises a stable nonpolyethylene containing dispersion of pigment particles and particles of a urethane polymer. In a preferred aspect of this embodiment, the composition further comprises a cross-linking agent to cross-link the urethane polymer within an individual layer of ink composition and between layers of ink or between ink and substrate. The term "stable" as used in this invention refers to the ability of the urethane polymer to exist as a dispersion with the pigment. Nonstable dispersions of ink tend to agglomerate or to coagulate while stable dispersions can exist as a suspendable mixture of pigment particles and particles of urethane polymer.

Although urethane polymers have been used as materials for pigment grinding, these urethane polymers have been hard materials used to help in the dispersion of pigments and have not been prepared from softer urethane polymers that are useful for adhesion of a composition to an elastomeric substrate, as disclosed in this invention. Preferably, the urethane polymers of this invention have a Shore A durometer (Type "A-2", Shore Instrument and Manufacturing Co., NY) value, as performed using ASTM D-2240 of less than about 35 and preferably a value greater than about 5. For purposes of this invention, the urethane polymer is stable as a dispersion with the pigment for at least about six hours after the urethane polymer and pigment are initially combined and preferably for at least about eight hours after they are initially combined.

The term "latex" is used herein to refer to an emulsion or a suspension of a synthetic rubber or polymer. The term "urethane adhesive" is used herein to refer to adhesives that demonstrate adhesive properties such as excellent sheer and peel results (i.e., at least about 100 gm/2.54 cm). The term "ink composition" is used in this invention to refer to compositions suitable for printing ink on a substrate where the composition contains visible pigment. The term "reactive particles of a urethane polymer" as used herein refers to the ability of the particles of the urethane polymer to be cross-linked in the presence of a cross-linking agent.

Urethane polymers are known and are commercially available for use as adhesives. Urethane polymers suitable for use in the present invention preferably comprise an aqueous suspension (i.e., latex) of a polymer having a number average molecular weight in the noncross-linked form of about 1,500 to about 50,000 and in a cross-linked form the urethane polymers of this invention are preferably in the range of about 50,000 to about 10,000,000 or more. The particle size of the polymer will generally range from about 0.01 micron to about 0.25 micron, and preferably about 0.01 to about 0.10 micron. In general, the urethane polymer contains preferably less than about 60 wt % polymer solids, based on the weight of the urethane polymer and preferably greater than 30 wt % polymer solids and typically about 30 wt % to about 60 wet %. Also preferably, the urethane particles used in this invention preferably have a density of greater than 8.1 lbs/gallon and preferably less than about 8.4 lbs/gallon.

In general, the urethane polymers that are useful in this invention include single-component water-compatible urethanes as well as blends of water-compatible urethanes. A variety of urethanes are known in the art that can be used in this invention. These include, but are not limited to, polyurethane dispersion adhesives such as those disclosed in U.S. Pat. No. 4,540,633 to Kucera, U.S. Pat. No. 4,147,679 to Scriven et al., U.S. Pat. No. 4,301,053 to Wolfrey, and U.S. Pat. Nos. 4,433,095 and 4,663,377 to Holmbach et al. Preferably, the urethane polymers are water-based urethane adhesives and preferred urethane polymers are those available from H.B. Fuller Co. (St. Paul, Minn.) and the subject of U.S. Pat. Nos. 5,494,960 and 5,532,058 to Rolando.

The urethane polymers preferably include a particle size that does not substantially interfere with the final resolution of the ink in its printed form. Preferably the urethane polymers are suitable for dry bonding, adhere well to a substrate, provide good clarity and are readily adapted for automation. Further, the preferred urethane polymers permit co-dispersion of the pigment in with the urethane polymer in an aqueous, or substantially aqueous dispersion. If water-based inks are needed, it may be necessary to use a water-based or water compatible urethane emulsion. Solvents can be present in the dispersion if they permit or do not interfere with the formation of a stable dispersion. For example, the aqueous dispersion can include polar solvents, including alcohols, as long as the dispersion maintains the characteristics of an aqueous solution.

Because dispersions of urethane polymers are prepared from small particles of urethane, a cross-linker can be used to link the urethane polymer molecules together to prevent redispersion of the urethane and failure of the ink bond. Preferably, the cross-linkers are chemical cross-linkers and preferable the cross-linkers are those that are capable of reacting with functional groups on the polymer to form a cross-linked urethane polymer adhesive. Particularly suitable cross-linkers include aminoplast resins, formaldehyde, phenolic resins, alkoxy silanes, organic polyisocyanates, carbodiimide materials and the like. Preferred cross-linkers include polyfunctional aziridines such as XR2990 cross-linker (H.B. Fuller Co., St. Paul, Minn.), isocyanates such as WD 6318 (Hexamethylene-1,6-diisocyanate H.B. Fuller Co.), polyisocyanates, such as WD 6314 (H.B. Fuller Co.), or the like. The presence of cross-linkers in the ink composition can improve water and alcohol resistance. While the ink compositions of this invention have improved durability resulting from the addition of the urethane polymer, durability and abrasion resistance is improved even more by the addition of a cross-linking agent that is compatible with the urethane selected.

For purposes of the present invention, particles of urethane polymers are incorporated in the ink composition in an amount from about 5 wt % to about 99 wt % by weight, preferably about 20 wt % to about 99 wt %, and most preferably from about 58 wt % to about 93 %, based on the final wet weight of the ink composition.

The ink compositions of this invention preferably include at least about 1% pigment particles by weight of the ink composition and preferably less than about 60% pigment particles by weight of the final ink composition. That is, the ink compositions can be lightly tinted or contain intense pigment color. Where the ink composition is used not as a tint, but as a vibrant ink, then the ink composition preferably includes up to about 60% pigment particles by weight in the final ink composition and preferably up to about 40% pigment particles by weight in the final ink composition. The urethane polymer is preferably present in the composition in at least about 5% by weight of the final ink composition. The urethane polymer can be added with pigment de novo to create an ink composition or the urethane polymer can be added to an existing ink to enhance the durability of the ink.

The liquid in the dispersion for the printing ink compositions of the present invention is preferably a liquid component or mixture of components that serves as an aqueous dispersing and carrying medium for the pigment particles of the printing ink and that also impart appropriate rheological properties such as plasticity, flow, viscosity, and the like to the printing ink. The liquid in the dispersion is typically present in an amount of about 30 wt % (i.e., by weight in the final ink composition) to about 93 wt % of the final ink composition. Those of ordinary skill in the art will recognize, in view of this disclosure, that there are a variety of combinations of pigment, dispersion liquid and urethane polymers will produce an ink composition suitable for printing on a flexible or elastomeric substrate.

The addition of urethane to a pigment composition can result in a viscous suspension. High loading of pigment, such as above 30 wt % of the ink composition can result in a composition that is too viscous for flexographic and gravure printing. Such pigment loading can require dilution of the overall mixture. In contrast, screen printing and letter press ink can be used at higher viscosities without compromising those printing processes. Viscosity can be tested using a variety of methods known in the art and preferred viscosity measurements can be taken using ASTM Designation D 1084-88 "Standard Test Methods for Viscosity of Adhesives." In general, the viscosity of the ink composition for flexographic applications is preferably between about 50 centipoise to about 200 centipoise but for gravure printing the viscosity of the ink can also be less than 50 centipoise.

Apart from the present invention, the components of the printing ink composition are conventional in nature. As indicated above, the liquid used to produce a dispersion is primarily aqueous in nature; however, solvents other than water can be included in the dispersion.

The pigments useful in this invention include both organic and inorganic pigments, which include, but are not limited to, monoarylide yellows, diarylide yellows, pyrazolones, bezimidazolones, toluidine red, naphthol red, lithol rubines, phthalocyanine blue and green, carbon blacks, titanium dioxide, zinc sulphide, calcium carbonate, China clay, and the like. Preferred ink compositions include water-based pigments that are commercially available including, but not limited to, water-based inks available from Werneke (Plymouth, Minn.), Akzo Nobel Inks (Longhorne, Pa.), Arcar (West Chicago, Ill.), and Colorcon, Corp. (West Point, Pa.).

Typically the printing ink composition will also contain binders, such as, for example, rosins and/or resins such as wood rosin, metallic resinates, maleic-modified rosins and resins such as, but not limited to, phenolic resins, alkyd resins, polyamide resins, acrylic and methacrylic resins, etc. The printing ink can also contain oils (such as, for example, soy bean oil), plasticizers, natural and/or synthetic waxes, driers, extenders, and the like.

The ink compositions of this invention have improved durability. The ink compositions are preferably abrasion resistant, showing abrasion resistance when stretched or deformed and have improved water-resistance as compared to formulations lacking the urethane polymer with or without cross-linking. Abrasion resistance can be tested in a variety of methods such as using a Sutherland Rub Tester (Danilee, Co., San Antonio, Tex.). There are a variety of abrasion testing regimes that can be performed using the Sutherland Rub Tester and a preferred method is provided in Example 3. An ASTM Standard Test Method using the Sutherland Rub Tester is also available as ASTM D 5264. Other abrasion testing can be performed and examples of other abrasion testing regimes include, but are not limited to a Taber Abraser (Taber Industries, Tonawano, N.Y.), using, for example, the ASTM Standard Test Method for Abrasion Resistance of Organic Coatings by the Taber Abraser (ASTM Designation D 4060-95). In another method, the abrasion resistance of the ink compositions of this invention coated on a flexible or elastomeric substrate can be tested using a finger rub test, such as that provided in Example 4. The term "abrasion resistance" for the ink compositions of this invention refers to ink compositions according to this invention that are able to withstand exposure to the Sutherland Rub Tester under the conditions of Example 3 for at least 6 cycles with less than about a 25% reduction in the printed image or able to withstand the Finger Rub Test, as provided in Example 4, for at least about 2 to about 4 hours with less than about 25% reduction in the printed image (for example, as measured by visual observation or as measured by a densitometer quantifying loss in print density).

The inks of this invention can be used in a variety of printing processes including, but not limited to, offset printing, rotogravure printing and flexographic printing as well as screen and rotary screen printing. Flexographic printing on thin, transparent, flexible or elastomeric polyurethane can present a challenge due to the extreme elasticity and low surface energy of the polyurethane. For this reason the flexible or elastomeric surfaces can be corona-treated, using methods known in the art to improve the surface energy of the substrate. Since most flexographic plates are made from polyurethanes, it is not possible to use solvents in ink that will swell the polymer and allow the pigment and binder to get strong anchorage to the substrate. The same solvents that enhance anchorage will destroy the flexographic plates. It is necessary to get ink adhesion another way. The present invention advantageously permits anchorage through the use of polyurethane adhesive mixtures in one or more layers of ink positioned on the substrate.

The flexible or elastomeric surface can be printed directly using flexographic printing or a variety of other printing methods with one or more successive ink compositions including those of the present invention as well as a variety of standard ink compositions in a variety of colors as prescribed by a particular printing process. Alternatively, the surface can be first treated with a lightly tinted ink composition according to this invention.

Referring now to FIG. 1, the flexible or elastomeric substrate 10 is preferably printed by adding a first layer of ink 12, prepared according to this invention, to the elastomeric substrate. Preferably, the first layer includes a urethane cross-linker and preferably the first layer of ink has a light tint. Preferably the light tint is due to the presence of white pigment in the ink composition. The term "lightly tinted" for the ink composition refers to less than about 10% pigment by weight of the final ink composition, and preferably less than about 5% pigment by weight of the final ink composition. This lightly tinted ink composition is first added to a flexible or to an elastomeric substrate. The ink composition containing the lightly tinted ink composition preferably comprises a stable aqueous dispersion of pigment particles and particles of a urethane polymer and also preferably includes a cross-linker capable of cross-linking the urethane polymer. Preferably the ink composition does not include polyethylene.

An image, such as lettering or a figure, is printed using flexographic printing, gravure, off-set printing or other printing methods using the ink compositions of this invention. The first layer of ink, according to this invention, 12 is preferably printed or coated directly onto the flexible or elastomeric substrate. Where the image is lettering, the first layer 12 preferably includes an ink composition that includes an aqueous dispersion of pigment particles and particles of a urethane polymer. Where the image is a multicolor image, the first layer 12 preferably comprises white or lightly tinted pigment particles, such that the first layer, when printed onto the substrate is visible to the eye. This layer can optionally include a cross-linker for the urethane and preferably this layer is either equivalent in size to the entire printed image or slightly larger than the printed image. Preferably the ink composition layered directly onto the substrate includes an aqueous dispersion of urethane particles and preferably also includes a cross-linker.

Where the image is multi-colored, one or more layers of ink in one or more colors are positioned over the first layer to form one or more pigmented layers of ink 14. The ink layers can be prepared using the ink compositions of this invention or the inks can be selected from commercially available aqueous or non-aqueous inks (i.e., non-water based inks). Where the ink layer employs an ink composition according to this invention, the layer can also optionally include a cross-linker for the urethane. The ink composition used for the multiple layers of color preferably includes the dispersion of pigment particles and particles of a urethane polymer. The ink composition of at least the last layer of ink applied to the image, i.e., the layer farthest from the substrate, preferably includes a cross-linker to cross-link the urethane polymer. Other ink layers can optionally include the particles of the urethane polymer and optionally include the cross-linker. Preferably, the top ink layer includes a cross-linker. Those of ordinary skill in the art will recognize that a variety of layering combinations are possible and that a variety of combinations, as contemplated in this invention, will improve the durability of an image on a flexible or elastomeric substrate.

Optionally, although pictured in FIG. 1, a layer of backsize or sealer 16 is preferably added at least over the image portion of the flexible or elastomeric substrate. Backsize or sealers are known and include, but are not limited to, polyvinyl carbamates, such as disclosed in U.S. Pat. No. 2,532,011 to Dahlquist, acrylate copolymers such as those of U.S. Pat. No. 2,607,711 to Hendricks, acrylate tetrapolymers, such as those of U.S. Pat. No. 3,011,988 to Luedke et al. or suitable fluorochemicals, such as those of U.S. Pat. No. 3,318,852 to Dixon, or mixtures thereof. Although the backsize layer does not substantially affect abrasion resistance or durability of the image, the backsize or seal layer 16 does protect the ink if heat seal processes are used. Also optionally, a polyurethane sealer such as a polyurethane adhesive including those of the HYDROFLEX family of film laminating adhesives (H.B. Fuller Co., St. Paul, Minn.) can be added as a clear layer over the printed image. In addition, a dulling agent can be provided in the last layer of ink or in the clear layer if a matte finish is desired.

Figure 2:
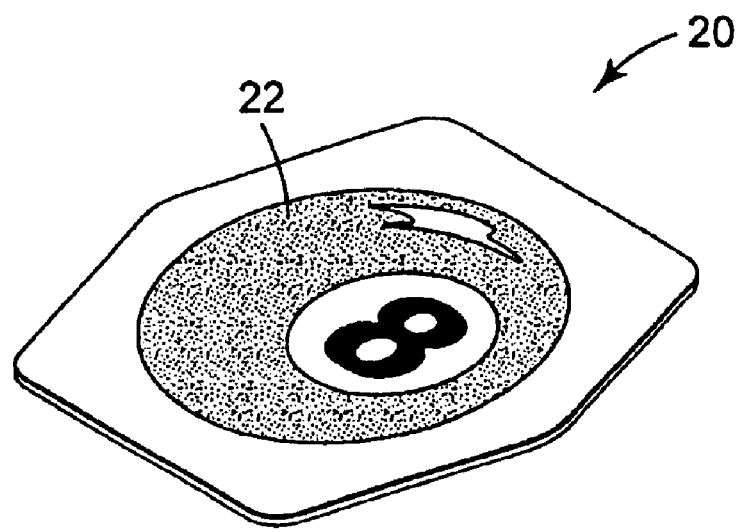
FIG. 2 is a transparent elastomeric-type bandage with an image printed using the ink compositions and methods of this invention.

FIG. 2 is a diagram of a bandage 20 having a flexible or elastomeric substrate. The bandage 20 comprises a printed image, in this case, a printed 8-ball image 22, where the printed image is prepared using an ink composition comprising a stable aqueous dispersion of pigment particles and particles of a urethane polymer. Preferably, the first ink composition positioned over the flexible substrate comprises the water-based urethane polymer and a cross-linker that can cross-link the water-based urethane polymer to further enhance water resistance. Preferably the first ink layer is printed in an area that is at least the size of the total printed image or preferably slightly larger. Over this layer is printed one or more layers of ink to produce the printed image. Where a multi-color image is created, the second layer can be a white ink, particularly where the elastomeric substrate is transparent and where, such as with a bandage, the image is preferably centered over the absorbent pad. The remaining inks used to create the image are standard commercially available inks or alternatively are inks prepared according to this invention.

There are a variety of other flexible or elastomeric substrates that can be printed with the ink compositions of this invention. Other examples include, but are not limited to, balloons, stickers, labels, temporary tattoos, gloves prepared from flexible or elastomeric materials, stretch bands, and a variety of flexible and/or elastomeric sheets, films, tapes, bags, and the like.

All references and publications cited herein are expressly incorporated by reference into this disclosure. Particular embodiments of this invention will be discussed in detail and reference has been made to possible variations within the scope of this invention. There are a variety of alternative techniques and procedures available to those of skill in the art which would similarly permit one to successfully perform the intended invention.

EXAMPLE 1

Various Ink Compositions with Urethane Dispersion

Various ink compositions were prepared and tested. All percentages are provided as weight to weight relative to the final weight of the ink composition.

Ink A
- 80% FM 4000-II UFR Black ink (Werneke Ink, Plymouth, Minn.)
- 19.6% HYDROFLEX WD-4007 Urethane Dispersion (H.B. Fuller Co., St. Paul, Minn.)
- 0.4% HYDROFLEX XR-2990 cross-linker (H.B. Fuller Co.)

The XR-2990 was added to the vortex of the WD-4007 urethane polymer slowly with moderate sheer stirring. Mixing was continued for one minute after addition of the XR-2990 was complete. 20 grams of the resulting mixture was added to 80 grams of the ink also with moderate sheer stirring. The resulting ink was coated onto corona treated (42 dynes/cm$^2$) polyurethane elastomeric film with a Pamarco hand proofer (Pamarco, Inc., Roselle, N.J.) fitted with a 200 Anilox metering roll. For comparison, 100% FM 4000-II UFR black ink (Comparative Ink I) was coated onto identical film in an identical manner.

Ink B
- 80% FM 4000-II UFR Black ink (Werneke)
- 19.6% HYDROFLEX WD-4008 Urethane Dispersion (H.B. Fuller Co.)
- 0.4% HYDROFLEX XR-2990 cross-linker (H.B. Fuller Co.)

The XR-2990 was added to the vortex of the WD-4008 urethane polymer slowly with moderate sheer stirring. Mixing was continued for one minute after addition of the XR-2990 was complete. 20 grams of the resulting mixture was added to 80 grams of the ink also with moderate sheer stirring. The resulting ink was coated onto corona treated (42 dynes/cm$^2$) polyurethane elastomeric film with a Pamarco hand proofer fitted with a 200 Anilox metering roll. For comparison, 100% FM 4000-II UFR black ink (Comparative Ink I) was coated onto identical film in an identical manner.

Ink C
- 80% HYDROFOIL Dense Black ink #1256 (Akzo Nobel Inks Corp. Langhorne Pa.)
- 19.6% HYDROFLEX WD-4007 Urethane Dispersion (H.B. Fuller Co.)
- 0.4% HYDROFLEX XR-2990 cross-linker (H.B. Fuller Co.)

The XR-2990 was added into the vortex to the WD-4007 urethane polymer slowly with moderate sheer stirring. Mixing was continued for one minute after addition of the XR-2990 was complete. 20 grams of the resulting mixture was added to 80 grams of the ink also with moderate sheer stirring. The resulting ink was coated onto corona-treated (42 dynes/cm$^2$) polyurethane elastomeric film with a Pamarco hand proofer fitted with a 200 Anilox metering roll. For comparison, 100% HYDROFOIL Dense Black ink #1256 (Comparative Ink II) was coated onto identical film in an identical manner.

Ink D
- 80% HYDROFOIL Dense Black ink #1256 (Akzo Nobel Inks Corp.)
- 19.6% HYDROFLEX WD-4008 Urethane Dispersion (H.B. Fuller Co.)
- 0.4% HYDROFLEX XR-2990 Cross-linker (H.B. Fuller Co.)

The XR-2990 was added into the vortex of the WD-4008 urethane polymer slowly with moderate sheer stirring. Mixing was continued for one minute after addition of the XR-2990 was complete. 20 grams of the resulting mixture was added to 80 grams of the ink also with moderate sheer stirring. The resulting ink was coated onto corona-treated (42 dynes/cm$^2$) polyurethane elastomeric film with a Pamarco hand proofer fitted with a 200 Anilox metering roll. For comparison, 100% HYDROFOIL Dense Black ink #1256 (Comparative Ink II) was coated onto identical film in an identical manner.

Ink E

Lightly tinted ink composition:
- 93.3% H.B. Fuller WD-4006 urethane polymer
- 1.9% XR-2990 cross-linker (H.B. Fuller Co.)
- 4.8% FLEXIVERSE II WFD-5006 white pigment dispersion (Sun Chemical Corp., Amelia Ohio) or 4.8% an ink in a different colored dispersion (Sun Chemical or Colorcon, West Point, Pa.)

The XR-2990 was added into the vortex of the WD-4006 urethane polymer slowly with moderate sheer stirring. Mixing was continued for one minute after addition of the XR-2990 was complete. The FLEXIVERSE WFD-5006 white pigment dispersion was added and mixed to a uniform appearance. This ink was printed as a solid mask image under all the printed area from a 400 Anilox roll. The term "Anilox" as used herein refers to the engraved steel roll used to meter ink to the plate cylinder of a flexographic press.

Ink F

White ink
- 81.7% H.B. Fuller WD-4006 urethane polymer
- 1.6% H.B. Fuller XR-2990 cross-linker
- 16.7% FLEXIVERSE II AFD-5006 white pigment (Sun Chemical Corp.)

The XR-2990 was added into the vortex of the WD-4006 urethane polymer slowly with moderate sheer stirring. Mixing was continued for one minute after addition of the XR-2990 was complete. The FLEXIVERSE WFD-5006 white pigment dispersion was added and mixed to a uniform appearance. This ink was printed as a solid mask image under all the printed area from a 400 Anilox roll.

Ink G
- 76.9% H.B. WD-4007 Urethane polymer
- 23.1% FLEXIVERSE II WFD-5006 white pigment dispersion (Sun Chemical Corp.)

The FLEXIVERSE WFD-5006 white pigment dispersion was added and mixed to produce a uniform mixture. The ink was printed as a solid mask image under all of the printed area from a 400 Anilox roll.

Ink H
- 66.7% H.B. WD-4007 Urethane polymer
- 33.3% FLEXIVERSE II WFD-5006 white pigment dispersion (Sun Chemical Corp.)

The resulting ink was printed onto corona-treated (34 dynes/cm$^2$) polyurethane elastomeric film with a Pamarco hand proofer fitted with a 200 Anilox metering roll. The ink was printed to demonstrate that higher loading of pigment could be used without interfering with flexo-printing processes.

Printing method for ink composition E, F and G:

Using an 8 station flexographic press. Station 1 used the white ink of composition E, Station 2 uses the composition of compositions F and G, Stations 3 through 6 employ colorprinting of cyan, magenta, yellow and black Colorcon No-Tox solvent (non-aqueous) based inks, generally an alcohol or glycol based ink (Colorcon) using 400 to 600 Anilox rolls with 100 line screen flexo-printing plates, station 7 and 8 are available for top coats as needed for the converting process.

EXAMPLE 2

Urethane Ink Composition and Methods of Use Printing

In this example, a urethane film positioned on a silicone release surface that was positioned on a paper liner was used as the substrate.

The urethane film (preferably 1.2 mil 30 micron film of ESTANE 58309 Urethane resin, B.F. Goodrich, Cleveland, Ohio) or carrier dressings prepared according to U.S. Pat. No. 5,531,855 to Heinecke et al.) was first printed with a tinted composition comprising 93.3% HB Fuller HYDROFLEX WD 4006, 1.9% HB Fuller HYDROFLEX XR 2990 and 4.8% SunChemical FLEXIVERSE II White WFD-5006. The tinted ink was positioned such that it extended beyond the printed area. A white ink of 81.7% HB Fuller HYDROFLEX WD4006, 1.6% HB Fuller HYDROFLEX XR 2990 and 16.7% Sun Chemical FLEXIVERSE II White WFD-5006 was applied slightly smaller than the color printed areas positioned over the base coat. All ink percentages are provided as weight to weight of the final ink composition. Other colored inks were printed in design or lettering using standard flexographic printing methods. A covering of a silicone/urethane backsize was applied over the entire surface of the printed product as described in U.S. Pat. No. 5,531,855 to Heinecke et al.

EXAMPLE 3

Abrasion Resistance Testing of Ink Compositions

Abrasion resistance was tested using a Sutherland Ink Rub Tester (Danilee Co., San Antonio Tex.). The method provides a quantitative method for evaluating samples for rub damage. The methods used in this example are those of ASTM-D5264-92 entitled "Standard Test Method for Abrasion Resistance of Printed Material by the Sutherland Rub Tester." The following modifications were made to the Sutherland Rub Tester method. A two pound weight (8.89 Newtons) was modified by adding 4 layers of 1/32" (0.079 cm)×2" (5.08 cm)×2" (5.08 cm) microfoam vinyl tape (Microfoam Surgical Tape, Minnesota Mining and Manufacturing, St. Paul, Minn.) interposed between 2 separate 2" (5.08 cm)×1" (2.54 cm)×1/8" (0.3175 cm) neoprene pads at each end of the rub weight. The entire 2" (5.08 cm)×4" (10.16 cm) surface was covered with 1 layer of microfoam tape. The printed test image was placed over the 1" (2.54 cm)×½ 1.27 cm) raised area at the center of the 2 lb. (8.89 Newtons, "N") weight. The force applied to the image was 2 lb per ½ in$^2$ or 4 psi or 2.76 N per cm$^2$. The area had a Shore A-2 durometer hardness of 15.

The image and weight rub against an area of lint free Twill Jean Cloth (available from Electron Microscopy Sciences, Fort Washington, Pa., #71750) moistened with about 1–2 cc per about 40 cm$^2$ of 0.5% Triton X-100 in water. One cycle of abrasion was one complete back and forth movement of the 2 lb (8.89 N) weight. Ink compositions with and without the urethane polymer and with or without the cross-linker were compared. Results indicated greatly improved resistance to rubbing when the urethane polymer containing ink compositions were used.

In one example, samples were printed on B.F. Goodrich #58309 urethane film using Colorcon ink printed according to standard flexographic methods using at least six different images. Results are summarized as the number of cycles to produce noticeable and significant image wear (generally until there was at least about a 25% decrease in the image density, as described supra).

All images were tested after printed on an elastomeric substrate such as that of U.S. Pat. No. 5,531,855 to Heinecke et al.

| Ink | Cycles |
| --- | --- |
| Colorcon Ink printed image only | 10–20 |
| Ink heated to 95° C. after printing to secure ink to substrate | 20–25 |
| Ink E (supra) positioned under a Colorcon printed image | 80–150 |

The resistance of the printed image to wet rub was over four times better than the best printing ink adhesion obtained without the urethane polymer base ink composition.

EXAMPLE 4

Ink Compositions Tested Using the Finger Rub Test

The printed image on a flexible or elastomeric substrate were affixed on the side of the interphlangeal joint between the distal phalanx and middle phalanx so that the thumb print area rubs on the surface of the printed image. Wear of the image was noted when visible loss of image quality was evident through lightening of the color of the image or by visualization of small areas that no longer had printing and therefore created an overall image that was aesthetically unacceptable. The time necessary to totally rub the image from the substrate was also noted. These times were indicative of printing durability and abrasion resistance.

This test offered a simple method for testing print durability under actual conditions of use. The position of the test sample in a high wear area, exposed to moisture, high flex, and high abrasion through contact of the affixed substrate with the thumb or with contact surfaces. Samples were tested over a variety of times and conditions; however, minimum times were between about 2 to about 4 hours. Ink Compositions cited are those provided in Example 1.

| Ink | Time to 25% wear | Time to 95% wear |
| --- | --- | --- |
| Comparative 1 on 42 dyne film 200 Anilox proof print | 60 min | 120 min |
| Ink A on 42 dyne film 200 Anilox | 720 min | >1440 min |
| Ink A on 34 dyne film 200 Anilox | NA | 840 min |
| Ink E on 42 dyne Colorcon ink printed image | 200 min | 1630 min |
| Comparative II on 42 dyne Colorcon ink printed image | 15 min | 30 min |
| Ink G on 34 dyne film Colorcon ink printed image | 120 min | 300 min |
| Ink E on 34 dyne Colorcon ink printed image | 240 min–360 min | 1320 min |
| Multi-layer ink composition of Ink E followed by Ink F on 34 dyne Colorcon ink printed image | 360 min–480 min | 1620 min |

Surface energy of the substrate was tested using ACU•DYNE Test Marker Pins commercially available from Diversified Enterprises (East Wallingford, Vt.) following ASTM D-2578 and procedures recommended by Diversified Enterprises.

Only ink compositions according to the present invention were able to withstand abrasion regimes and conditions that were resistant to extended abrasion times.

EXAMPLE 5

Ink Compositions Tested for Stretch Resistance

Ink compositions were tested on elastomeric substrates (i.e., substrates that could stretch or deform to greater than or equal to about 5% of their original length in at least one direction). Samples were printed onto the substrate and the sample was then stretched and tested for durability using the Sutherland test of Example 3 with the following modification. A 2.5 in$^2$ (6.35 cm$^2$ test sample was stretched to either 2.75 inches (6.985 cm, 10% stretch), 3.0 inches (7.63 cm, 20% stretch) or 3.25 inches (8.255 cm, 30% stretch). The stretched portion was placed over the raised area at the center of the 2 lb. (8.89 N) weight. Results are provided below as the number of cycles needed to visibly decrease image density by about 25%.

|  | Percent Stretch | | |
| --- | --- | --- | --- |
| Ink | 10% | 20% | 30% |
| Colorcon ink | 15 | 7.5 | 1 |
| Ink E on 42 dyne Colorcon ink printed image | 60 | 40 | 20 |

Visual examination of the printed image using an ink composition without urethane polymer demonstrated that stretching of the printed substrate caused the printed image to crack and was readily rubbed off after stretching. The use of urethane polymer ink compositions as a layer on the elastomeric substrate improved the rub resistance 4 to 20 times when the substrate was stretched. The improvement was greatest at 30% stretch of the stretch levels tested. This amount of stretch is common for example, for bandages positioned on hand and knuckle areas. These values are consistent in the rub test with values shown in the Sutherland rub test.

It will be appreciated by those skilled in the art that while the invention has been described above in connection with particular embodiments and examples, the invention is not necessarily so limited and that numerous other embodiments, examples, uses, modifications and departures from the embodiments, examples and uses may be made without departing from the inventive scope of this application.

What is claimed is:

1. A method for improving durability of an image on an elastomeric bandage comprising:
coating an imagewise layer of a urethane polymer-containing ink composition onto an elastomeric substrate, which forms a part of the elastomeric bandage, wherein the urethane polymer comprises a number average molecular weight in the noncross-linked form of about 1,500 to about 50,000; and further wherein the composition comprises urethane polymer particles leaving a particle size of 0.01 micron to 0.25 micron.

2. The method of claim 1 wherein the urethane polymer-containing ink composition is a water-based composition comprising a dispersion of pigment.

3. The method of claim 1 wherein the urethane polymer-containing compound further comprises a cross-linker to cross-link the urethane polymer.

4. A method for printing an image on an elastomeric bandage comprising:
printing an image onto an elastomeric substrate, which forms a part of the elastomeric bandage, using at least one ink composition comprising a stable nonpolyethylene containing aqueous dispersion of pigment and particles of a urethane polymer; wherein the particles of the urethane polymer have a particle size of 0.01 micron to 0.25 micron.

5. The method of claim 4 further comprising the step of coating a layer of a urethane polymer-containing composition onto the elastomeric substrate before the printing step.

6. The method of claim 4 wherein the urethane polymer comprises a number average molecular weight in the noncross-linked form of about 1,500 to about 50,000.

7. The method of claim 5 wherein the urethane polymer-containing compound of the coating step further comprises a cross-linker to cross-link the urethane polymer.

8. The method of claim 4 wherein the ink composition further comprises a cross-linker to cross-link the urethane polymer.

9. The method of claim 4 wherein the ink composition is provided in at least one layer of ink in the printed image.

10. The method of claim 4 wherein at least one ink composition comprises a dispersion of white pigment.

11. The method of claim 4 wherein the at least one ink composition comprises at least one layer of ink in the image.

12. The method of claim 4 wherein the at least one ink composition is in the last ink layer printed in the image.

13. A method for printing an image on an elastomeric bandage comprising:
printing a first layer of ink onto an elastomeric substrate, which forms a part of the elastomeric bandage, the first layer of ink comprising a stable aqueous dispersion of pigment and particles of a urethane polymer; and
printing an image over the first layer of ink wherein the last layer of ink, farthest from the substrate, comprises a stable aqueous dispersion of pigment and particles of a urethane polymer; wherein the particles of the urethane polymer have a particle size of 0.01 micron to 0.25 micron.

14. The method of claim 13 wherein at least one layer of ink is printed using a nonaqueous-based ink.

15. The method of claim 13 wherein the ink composition in the first layer of ink further comprises a cross-linker to cross-link the urethane polymer.

16. The method of claim 13 wherein the first layer comprises an ink comprising a white pigment.

17. The method of claim 13 wherein an opaque layer of white pigment is disposed between the first layer of ink and the image.

18. The method of claim 13 wherein the image is printed with an ink composition comprising a stable aqueous dispersion of pigment and particles of a urethane polymer.

19. The method of claim 13 wherein the last layer of ink, farthest from the substrate, further comprises a cross-linker to cross-link the urethane polymer.

20. The method of claim 13 wherein the image is covered with a coating comprising a backsize or sealer.

21. The method of claim 13 wherein the sealer is a urethane polymer adhesive.

22. The method of claim 4 wherein the bandage comprises the elastomeric substrate and an adsorbent pad.

23. The method of claim 22 wherein the image is printed over the adsorbent pad.

24. The method of claim 4 wherein the elastomeric substrate is selected from a group consisting of polyurethane, elastomeric polyethylene, low density polyethylene and a nonwoven elastomeric web.

25. A method for limiting abrasion of an ink on an elastomeric bandage comprising:
applying at least one ink composition comprising a water-based dispersion of a urethane polymer to an elastomeric substrate, which forms a part of the elastomeric bandage, in an imagewise fashion; wherein the dispersion of a urethane polymer comprises urethane polymer particles having a particle size of 0.01 micron to 0.25 micron.

26. The method of claim 25 wherein the composition is an ink composition comprising a stable aqueous dispersion of pigment and particles of a urethane polymer and a cross-linker to cross-link the urethane polymer.

27. The method of claim 25 wherein the at least one ink composition of the printing step comprises a stable aqueous dispersion of pigment and particles of a urethane polymer and a cross-linker to cross-link the urethane polymer.

28. The method of claim 25 wherein the printing step is selected from the group consisting of rotogravure printing, flexographic printing and offset printing.

29. The method of claim 25 wherein the elastomeric substrate is selected from a group consisting of polyurethane, elastomeric polyethylene, low density polyethylene, and a nonwoven elastomeric web.

30. The method of claim 25 wherein the composition comprises a water-based pigment.

31. The method of claim 25 wherein the water-based pigment is a white pigment.

32. An elastomeric bandage comprising a printed image wherein the printed image is prepared from at least one ink composition comprising a stable aqueous dispersion of pigment and particles of a urethane polymer; wherein the particles of a urethane polymer have a particle size of 0.01 micron to 0.25 micron.

33. The elastomeric bandage of claim 32 wherein the at least one ink composition further comprises a cross-linker to cross-link the urethane polymer.

34. The elastomeric bandage of claim 32 wherein the bandage further comprises a pad.

35. The elastomeric bandage of claim 34 wherein the image is printed over the pad.

36. The method of claim 1 wherein the polymer particles have a particle size of 0.01 micron to 0.10 micron.

37. The method of claim 4 wherein the polymer particles have a particle size of 0.01 micron to 0.10 micron.

38. The method of claim 13 wherein the polymer particles have a particle size of 0.01 micron to 0.10 micron.

39. The method of claim 25 wherein the polymer particles have a particle size of 0.01 micron to 0.10 micron.

40. The bandage of claim 32 wherein the polymer particles have a particle size of 0.01 micron to 0.10 micron.

* * * * *

UNITED STATES PATENT AND TRADEMARK OFFICE
CERTIFICATE OF CORRECTION

PATENT NO. : 6,905,732 B1  
DATED : June 14, 2005  
INVENTOR(S) : Dunshee, Wayne K.

It is certified that error appears in the above-identified patent and that said Letters Patent is hereby corrected as shown below:

<u>Title page,</u>  
Item [57], ABSTRACT,  
Line 3, after "polymer" insert -- . --.

<u>Column 6,</u>  
Line 33, delete "wet" and insert -- wt --, therefor.

<u>Column 7,</u>  
Line 25, after "93" insert -- wt --.

<u>Column 10,</u>  
Line 43, delete "absorbent" and insert -- adsorbent --, therefor.

<u>Column 13,</u>  
Line 46, delete "½" and insert -- ½ --, therefor.  
Line 46, delete "1.27 cm)" and insert -- (1.27 cm) --, therefor.

Signed and Sealed this

Fifteenth Day of November, 2005

JON W. DUDAS  
*Director of the United States Patent and Trademark Office*